United States Patent [19]

Turner et al.

[11] 4,083,228
[45] Apr. 11, 1978

[54] GAS COMPARISON PYCNOMETER

[75] Inventors: Philip L. Turner, Del Mar; Robert W. Gilkey, San Diego; Peter L. Lagus, Olivenhain, all of Calif.

[73] Assignee: Systems, Science and Software, La Jolla, Calif.

[21] Appl. No.: 787,768

[22] Filed: Apr. 15, 1977

[51] Int. Cl.² .............................................. G01N 9/26
[52] U.S. Cl. .................................... 73/32 R; 73/38; 73/149
[58] Field of Search .................... 73/32 R, 37, 38, 149

[56] References Cited

U.S. PATENT DOCUMENTS

| | | | |
|---|---|---|---|
| 3,060,724 | 10/1962 | Smith et al. | 73/32 R |
| 3,113,448 | 12/1963 | Hardway et al. | 73/149 |
| 3,255,122 | 6/1966 | Constabaris et al. | 73/38 |

FOREIGN PATENT DOCUMENTS 393,595  12/1973  U.S.S.R. ................................. 73/149

Primary Examiner—Richard C. Queisser
Assistant Examiner—Stephen A. Kreitman
Attorney, Agent, or Firm—Fitch, Even, Tabin & Luedeka

[57] ABSTRACT

A pycnometer apparatus is disclosed for accurately determining the volume of a condensed material sample. Equal free space volumes are established in a pair of gas filled chambers before and after insertion of a sample of the condensed material within one of the chambers. The volume of the sample receiving chamber is increased to maintain equal free space volumes after the sample is inserted, the adjusted increase in volume providing a highly accurate determination of the volume of the sample. The apparatus may also be employed to determine the compressibility or the porosity of a material sample.

8 Claims, 5 Drawing Figures

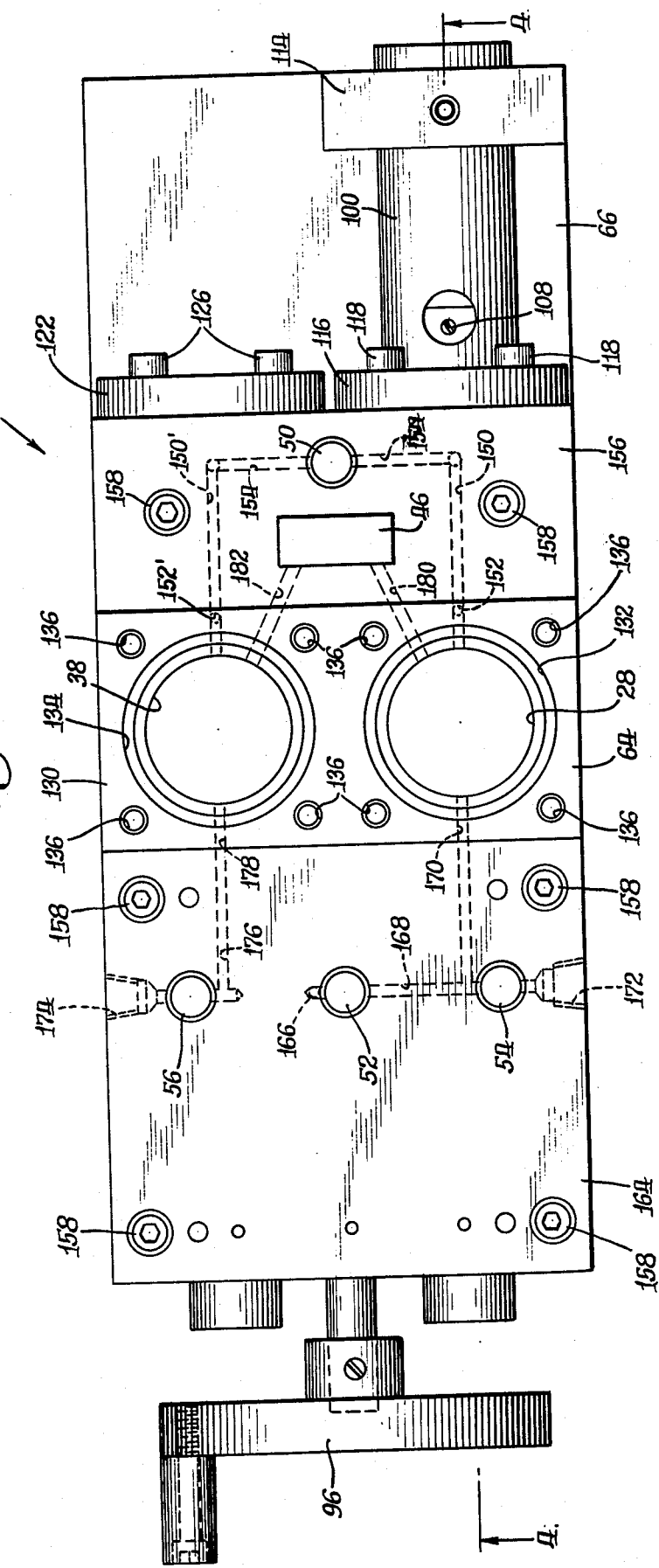

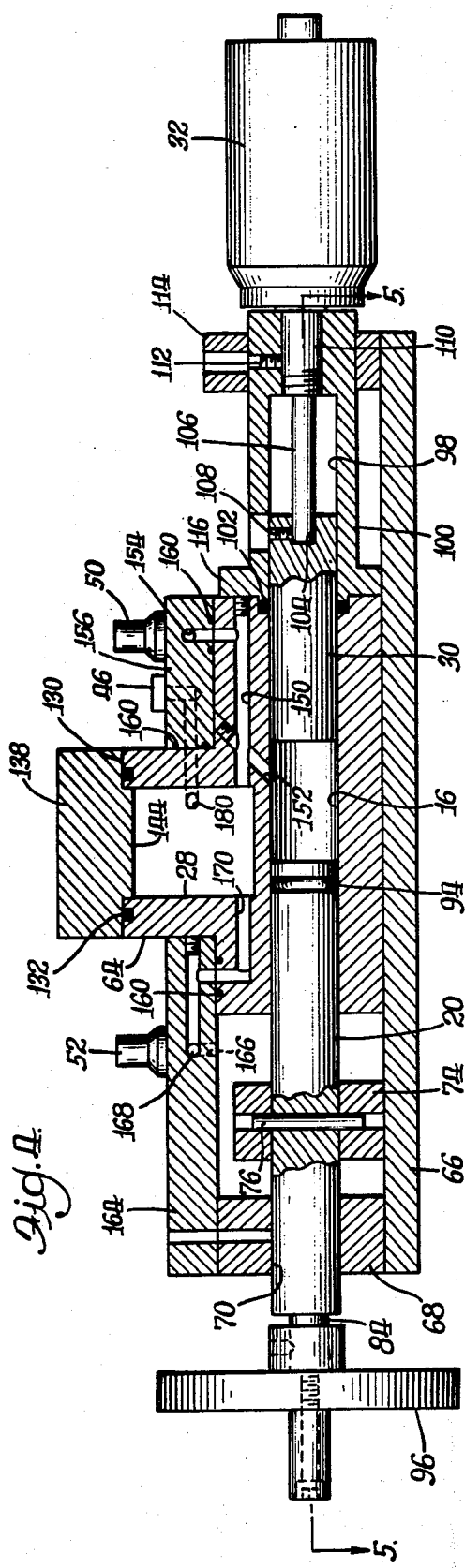

GAS COMPARISON PYCNOMETER

The present invention relates generally to apparatus for determining the volume of a condensed material substance, and more particularly to a novel gas comparison pycnometer for determining the volume of a condensed material sample wherein equal free space volumes are maintained between a reference chamber and a sample receiving chamber throughout the sample volume determination, with the increase in volume of the sample receiving chamber necessary to maintain equal free space volume providing a highly accurate measurement of the volume of the sample.

The density of a substance is a fundamental property and for a crystalline substance is characteristic of that substance. As such, the density of a substance is a valuable diagnostic property and thus should be carefully determined. An accurate determination of density requires considerable care. Thus, the numerous possibilities for error must be guarded against. Among the more serious of the errors which can occur in determining density are the errors inherent in the method used, errors arising from inhomogeneity of the sample, and errors arising from the observer himself. Because some determinative methods are inherently more precise than others, it is important to select the technique that is best suited to give accurate results with the material available.

It is often difficult to obtain large portions of homogeneous material even of a mineral that is available in considerable amountes due to the inclusion of foreign material within the mineral. In general, therefore, best results are obtained by working with small amounts of material chosen as carefully as possible, preferably, in the case of solids or powders, small grains whose purity can be controlled by microscopic examination.

Of the numerous known methods available for determining the density of solids, three are particularly suitable for minerals. In a first method, the weight of the mineral is measured directly, the volume being measured by the principle of Archimedes. In a second method, the density is measured by direct comparison with heavy liquids, this normally being termed the suspension method. By a third method, the weight is measured directly, and the volume is inferred using a liquid or gas pycnometer.

The first method noted determines the volume of a mineral specimen by measuring the apparent loss of weight when a weighed fragment is immersed in a suitable liquid. This method is one of the simplest for determining the density of minerals, and if homogeneous pieces of sufficient size are obtainable it is one of the most accurate. A number of special balances have been developed for direct and rapid determination of density by the Archimedes method, the best known being the Jolly balance, as improved by Kraus.

In the second method noted, i.e. using heavy liquids, the grains of a specimen are immersed in a suitable liquid which is gradually diluted or made more dense as necessary to maintain the sample grains in a state of equilibrium within the liquid, neither floating or sinking. The density of the liquid at equality between the liquid and solid is determined by one of the standard procedures, generally by using a Westphal balance or by the equivalent procedure of weighing a plumb bob in air, in water, and in liquid.

The third noted method to infer the density of an object is by means of its primary definition as mass per unit volume. This requires an accurate determination of both mass and volume. Of the two quantities, mass is by far the easier to determine with high precision. Most commercially available balances possess a precision of greater than 1 part in 10,000. The determination of volume is not as readily determinable. If the substance being studied can be machined to a known geometrical shape a reliable volume can usually be obtained. For solid objects of irregular shape of for powders, volume determination is the limiting factor in the determination of the sample density. These volumes must be determined using either a liquid or gas pycnometer.

A liquid pycnometer operates on the principle that the volume of a known weight of solid is determined from the weight of the liquid displaced. Because of the difficulty in obtaining highly accurate results with a liquid pycnometer, it has been found best to avoid the liquid pycnometer technique if another method is available which will yield the accuracy required. For certain materials, however, such as friable fine-grained clays, the liquid pycnometer method may be the only usable method.

Volume determination by means of a gas generally yields better precision than that obtained with a liquid. The basis of all gas comparison pycnometry is some from of the gas law. For low pressures and quasi-static processes it is sufficient to consider a gas law of the form of:

$$PV = NRT$$

where
 $P$ = pressure
 $V$ = volume
 $N$ = number of moles of gas
 $R$ = gas constant
 $T$ = absolute temperature By pressurizing some type of sample container with and without a sample present, it is possible to infer sample volumes utilizing the relationship embodied in the above gas law equation either by noting a pressure change and keeping volumes constant, or keeping pressure constant and changing the sample container volume.

Commercially available gas comparison pycnometers can typically measure volumes to plus or minus ($\pm$) 0.1 cc. However, higher precision is desirable since volume uncertainty is the limiting factor in the determination of density. Three major criticisms of known commercially available gas comparison pycnometers can be made. Firstly, some devices require that the ideal gas law be precisely obeyed. Any departure from ideality of the gas being used results directly in an uncertainty in the inferred volume. Secondly, many devices are not stable against thermal variations. Changes in room temperature due to ambient variations can influence the pressure measured in the sample chamber. This in turn can cause a spurious variation in measured volume. Thirdly, in the balanced or zero condition, the number of moles of gas is different from that in the pycnometer when a sample is present. Thus, volumes are not calculated from measurements made under identical conditions.

One of the primary objects of the present invention is to provide a novel gas pycnometer apparatus for determining the volume of a condensed material sample which overcomes the disadvantages found in the prior art methods and gas pycnometers, the apparatus of the instant invention providing highly precision volume inferences of condensed materials such as solids, powders and liquids provided the vapor pressure of the liquid samples is properly accounted for.

Another object of the present invention is to provide an improved gas comparison pycnometer which allows rapid measurement of the volumes of condensed material samples with a precision of ±0.001 cc. Coupled with a precise measurement of mass, the densities of condensed materials can be inferred within 0.002 gm/cc.

A more particular object of the present invention is to provide a gas pycnometer apparatus wherein equal free space volumes are established within two substantially equal but variable volume gas containing chambers before and after a sample of condensed material is inserted within one of the chambers, and wherein means in the form of a volume compensating piston is provided for increasing the volume of the sample receiving chamber to maintain equal free space volume therebetween, such change in volume providing a highly accurate determination of the sample volume.

A feature of the present invention lies in the provision of a gas pycnometer apparatus having substantially equal volume chambers each of which has a primary piston axially movable therein, one of the chambers being adapted to receive a sample specimen therein of unknown volume and having a volume compensating piston axially movable therein, and the other chamber acting as a reference chamber and having a dummy piston disposed therein, the various elements of the apparatus having high thermal conductivity and being disposed to provide thermal symmetry about a vertical plane equidistantly spaced between the chambers of the apparatus so as to reduce the temperature sensitivity of the apparatus.

Further objects and advantages of the present invention, together with the organization and manner of operation thereof, will become apparent from the following detailed description of the invention when taken in conjunction with the accompanying drawings wherein like reference numerals designate like elements throughout the several views, and wherein:

FIG. 3 is a top plan view of the gas pycnometer of FIG. 1 but with the outer casing, chamber covers, micrometer and null gauge removed;

FIG. 4 is a vertical sectional view taken substantially along line 4—4 of FIG. 3; and FIG. 5 is a horizontal sectional view taken substantially along line 5—5 of FIG. 4.

Figure 1:
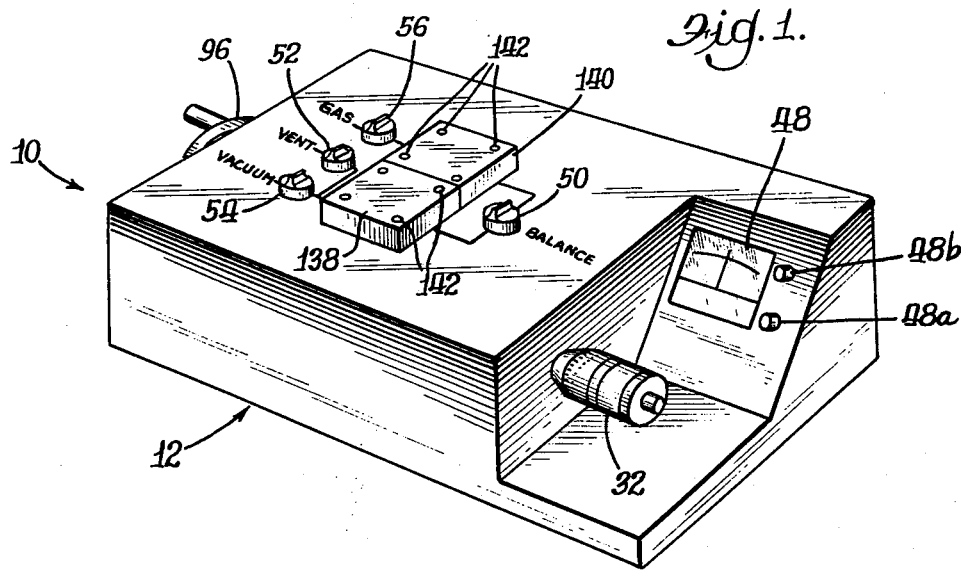
FIG. 1 is a perspective view of a gas pycnometer apparatus constructed in accordance with the present invention.
Figure 2:
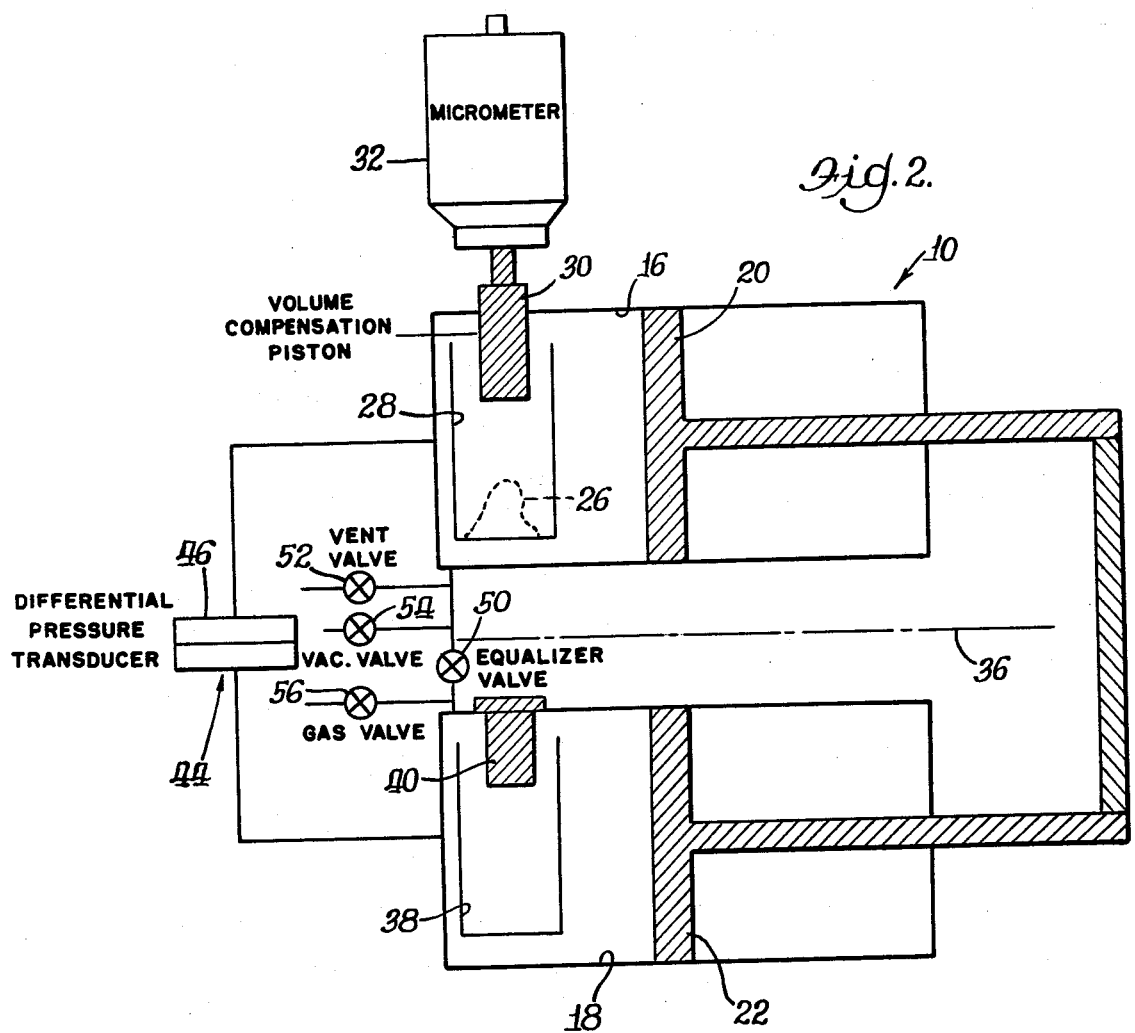
FIG. 2 is a schematic diagram of the gas pycnometer of FIG. 1.

Referring now to the drawings, and in particular to FIGS. 1 and 2, a gas pycnometer apparatus constructed in accordance with the present invention is indicated generally at 10. The pycnometer apparatus 10 includes a generally rectangular casing, indicated generally at 12, which houses the various components of the pycnometer and provides a compact and portable apparatus. The various components of the gas pycnometer apparatus 10 and their manner of operation will be briefly described in conjunction with FIG. 2 which schematically illustrates the operative relationship of various components in a manner to facilitate determination of the volume of a condensed material sample. As used herein, the term "condensed material" refers to substantially any material sample and includes solids, powders and liquids provided the vapor pressure of the liquid sample is properly accounted for during volume determination. As will become more apparent hereinbelow, the pycnometer apparatus 10 also lends itself to the determination of compressibility and thus the modulus of elasticity of a solid substance, as well as providing a means by which the porosity of a sintered material may be determined.

Referring to FIG. 2, the gas pycnometer apparatus 10 includes a pair of substantially equal volume chambers 16 and 18 each of which is adapted to receive a gas therein and has primary piston means in the form of a primary piston, indicated at 20 and 22, respectively, axially slidable therein between outward and inward positions to selectively compress the gas therein. The chamber 16 is adapted to receive a material sample therein and may be termed the sample receiving chamber. The chamber 18 may be termed the reference chamber and its associated piston 22 may be termed the reference piston. The pistons 20 and 22 are of equal diameter and are interconnected to facilitate simultaneous axial movement of the pistons within their respective chambers, thus eliminating the need for individual precision control of the pistons 20 and 22 between their outward and inward positions as has heretofore been required in the known gas pycnometer apparatus. The gas introduced into the chambers 16 and 18 may comprise any dry gas. One gas found particularly suitable for use in the gas pycnometer apparatus 10 is helium which rapidly reaches thermal equilibrium.

The sample chamber 16 is adapted to receive a sample, such as indicated at 26, of a condensed material such as a solid, powder or liquid substance the volume of which is to be measured by the pycnometer for purposes of inferring the density of the material substance. The sample 26 may have substantially any geometrical configuration making the need for precision machining of the sample unnecessary. To facilitate retention of the sample 26 within the chamber 16, a sample receiving chamber 28 is provided in communication with the chamber 16 so as to form a part of the sample chamber 16. Auxiliary means in the form of a volume compensation piston 30 is operatively associated with the chamber 16 so as to intrude the chamber 16 in a manner to selectively vary the free space volume of the chambers 16 and 28. The volume compensation piston 30, which may alternatively be termed an auxiliary piston, is adapted for selective incremental movement through measuring means in the form of a conventional micrometer adjustment 32 so as to provide highly accurate variation of the free space volume of the chamber 16 during operation of the pycnometer apparatus 10.

An important feature of the gas pycnometer apparatus 10 is the arrangement of the chambers 16 and 18 and the associated components symmetrically about a vertical plane containing the longitudinal axis of the apparatus, as represented by the line 36 in FIG. 2, to provide thermal symmetry. By providing such thermal symmetry, adverse temperature variations between the chambers 16 and 18 and their associated components are virtually eliminated. To this end, the chamber 18 includes and is in communication with the chamber 38 having substantially identical configuration and placement relative to chamber 18 as the sample receiving chamber 28 has to the chamber 16. A fixed piston 40 intrudes the chamber 18 and has a configuration substantially identical to the portion of the piston 30 which normally intrudes the chamber 16. The pressurizing pistons 20 and 22 and the volume compensating pistons 30 and 40 are made from stainless steel to minimize wear at the sealing surfaces and are preferably made from the same piece of material. These four parts are spatially arranged to provide structural symmetry about the longitudinal axis 36 of the pycnometer. The materials from which the various components of the pycnometer apparatus 10 are made preferably possess high thermal conductivity so as to substantially reduce the temperature sensitivity of the apparatus.

The gas pycnometer apparatus 10 includes means, indicated generally at 44, for monitoring the pressure difference between the chambers 16 and 18. In the illustrated embodiment, the pressure differential monitoring means 44 comprises a conventional differential pressure transducer 46 which is connected to the chambers 16 and 18 and to a conventional differential pressure readout gauge 48 (FIG. 1) mounted within the casing 12 so as to be readily readable. The gauge 48 facilitates the establishment of equal pressures within the chambers 16 and 18 by indicating any pressure difference between chambers. When the pointer of the gauge 48 is disposed on the zero or null pressure differential indicator marking, the pressures within the chambers 16 and 18 are equal. An "on-off" control knob 48a for energizing gauge 48, and a scale adjustment knob 48b are mounted adjacent gauge 48 as shown in FIG. 1.

The chambers 16 and 18 are connected through an equalizer or balance valve 50 which, when open, causes an equalizing of pressure within the chambers 16 and 18. A vent valve 52 is connected to the chambers 16 and 18 and is adapted to vent the chambers when the valve 50 is open and thus equalize the pressures within the chambers 16 and 18 at atmospheric pressure. A vacuum valve 54 is also connected to the chambers 16 and 18 and facilitates evacuation of the chambers 16 and 18 when the valve 50 is open. A gas valve 56 is also in communication with the chambers 16 and 18 and provides means for connecting the chambers 16 and 18 to a source (not shown) of a predetermined gas, such as helium, the gas valve 56 also being employed in conjunction with the vent valve 52 or vacuum valve 54 as necessary to introduce the predetermined gas into the chambers 16 and 18.

In carrying out the method for determining the volume of the condensed material sample 26, the chambers 16 and 18 are first adjusted to have equal free space volume without the sample 26 disposed within the sample chamber 28. In initially preparing the apparatus, the chambers 16 and 18 may be vented by opening the balance valve 50 and the vent valve 52 to introduce air into the chambers 16 and 18 under atmospheric conditions whereafter the valves 50 and 52 are closed to confine the gas within the chambers 16 and 18. Alternatively, the balance valve 50 may be opened and the chambers 16 and 18 connected to vacuum by opening the vacuum valve 54 to exhaust gases initially within the chambers 16 and 18. After evacuating the chambers 16 and 18, the valve 56 may be opened to introduce a predetermined gas such as helium into the chambers 16 and 18. This is done during initial establishment of equal free space volumes within the chambers 16 and 18 and also after the sample 26 is introduced into the sample chamber 28, as will be described.

After introducing a gas, such as helium, into the chambers 16 and 22 and with the valves 50, 52, 54 and 56 closed, the pistons 20 and 22 are moved from rearward positions forwardly equal distances within the respective chambers 16 and 18. If there is a pressure differential between the chambers 16 and 18 and detected by the differential pressure transducer 46 and indicated by the differential pressure indicator gauge 48, the auxiliary piston 30 is adjusted through the micrometer 32 inwardly or outwardly as necessary to reduce the differential pressure to zero and thus equalize or approximately equalize the free space volumes within the chambers 16 and 18. The chambers 16 and 18 are then cross-vented by opening the valve 50 and the pressurizing pistons 20 and 22 are moved to outward positions. The pistons 20 and 22 are moved between repeatable outward or inward positions as determined by built-in outer and inner stops at each movement thereof during operation, as will be described hereinafter.

With the pistons returned to outward positions within the chambers 16 and 18 as determined by the outer stop, the equalizer or balance valve 50 is closed. The pistons are then again moved forwardly equal distances as determined by the inner stop. If a differential pressure is found to exist after the second forward movement of the pistons 20 and 22, the auxiliary piston 30 is again adjusted to establish a zero or null differential pressure reading at the gauge 48. The balance valve 50 is then opened again and the pistons 20 and 22 are returned to their outward positions. This process is repeated until the differential pressure reads zero when the pistons are brought to their inward positions within their respective chambers 16 and 18, thus indicating equal free space volumes within the chambers 16 and 18.

After establishing equal free space volumes in the chambers 16 and 18 as described, the sample 26 is introduced into the sample chamber 28 and the chamber 28 again sealed. If helium or a gas other than air is being used as the gas in the chambers 16 and 18, the chambers are again evacuated and the selected gas, i.e. helium, is introduced into the chambers. The pistons 20 and 22 are then moved equal distances inwardly within the chambers to pressurize the chambers in the manner as aforedescribed. Due to the presence of the sample 26, a differential pressure will exist between the chambers 16 and 18 which requires adjustment of the volume compensating piston 30 through the micrometer 32. After adjustment of the volume compensating piston 30, the balance valve 50 is opened to cross-vent the chambers 16 and 18 whereafter the pistons 20 and 22 are withdrawn to their outer positions. The balance valve 50 is then closed and the pistons again move forwardly and the volume compensating piston 30 again adjusted if any differential pressure should be indicated between the chambers 16 and 18. This process is repeated until the differential pressure remains zero with the pistons 20 and 22 disposed in both forward and rearward positions within the chambers 16 and 18, thus indicating equal free space volumes within the chambers.

The adjustment of the volume compensating piston 30 necessary to reestablish equal free space volume within the chambers 16 and 18 after inserting the sample 26 therein provides a direct indication of the volume of the sample 26. The calculation of the volume of the sample 26 under conditions of equal free space volumes within the chambers as thus described provides a relatively quick and highly efficient and accurate method of establishing the volume of an irregularly shaped solid or powdered sample from which the density of the sample may be inferred with high accuracy. In accordance with the method of the present invention, rapid measurement of the volumes of liquid samples and irregularly shape solids and powders may be determined with a precision of ± 0.001 cc. Such volume measurement, coupled with a precise measurement of mass, allows the densities of condensed materials to be inferred within 0.002 gm/cc.

Referring now to FIGS. 3, 4 and 5, taken in conjunction with FIG. 1, for a detailed description of the gas pycnometer apparatus 10, the chambers 16 and 18 are formed in housing means in the form of a cylinder block 64 which is secured to the upper surface of a rectangular base plate 66. The cylinder block 64 is preferably made of aluminum or other suitable material of high thermal conductivity to obtain rapid temperature equilibrium between the chambers 16 and 18. The chambers 16 and 18 comprise parallel equal diameter cylindrical bores formed through the cylinder block 64 parallel and symmetrical to the longitudinal axis thereof.

The chambers 16 and 18 slidingly receive the pistons 20 and 22, respectively, which are of equal diameter and have their outer ends supported by and guided within a guide block 68 secured to the base plate 66 in upstanding relation thereon. The guide block 68 has parallel bores 70 and 72 formed therein to receive and support the associated pistons 20 and 22 in sliding relation therethrough.

To effect selective but equal movement of the pistons 20 and 22 within their respective chambers 16 and 18, the pistons are secured to a crosshead 74 through a pair of retaining pins 76. A crosshead nut 78 is retained within a central bore 80 in the crosshead 74 and has an internal threaded bore 82 therethrough which threadedly receives the external thread on a crosshead shaft 84 so that rotation of the crosshead shaft will effect selective movement of the crosshead 74 and a corresponding movement of the pistons 20 and 22. The crosshead shaft 84 has its forward end rotatable within a bearing 86 disposed within a bore 88 within the cylinder block 64, and has its rear end extending through and rotatably supported within the guide block 68 by a bearing 90. A pair of thrust washers 92 are disposed between the bearings 86 and 90 and suitable shoulder surfaces formed on the crosshead shaft 84 to retain the crosshead shaft in fixed axial position between the cylinder block and the guide block. An annular seal 94 is received within a suitable annular groove in the forward end of each of the pistons 20 and 22 to effect suitable sealing between the pistons and the bores defining the chambers 16 and 18. A handcrank 96 is suitably secured to the outer end of the crosshead shaft 84 and is manually manipulatable to rotate the crosshead shaft and effect simultaneous axial movement of the pistons 20 and 22.

As described, the pistons 20 and 22 are moved between repeatable outward and inward positions within the respective chambers 16 and 18 by rotation of the crosshead shaft 84. To this end, the crosshead 74 which carries the pistons 20 and 22 may be moved by rotation of crosshead shaft 84 between positions abutting opposed end surfaces 64a and 68a on the cylinder block 64 and guide block 68, respectively, as shown in FIG. 5. Alternatively, mechanical stops (not shown) could be mounted on the surfaces 64a and 68a to provide the desired limits of travel of crosshead 74.

The volume compensating or auxiliary piston 30 comprises a cylindrical piston which is axially slidably supported within the end of the chamber 16 opposite the piston 20. The volume compensating piston 30 has a length suitable to extend within the chamber 16 and has an outer end slidingly received within a cylindrical bore 98 in a micrometer support tube 100. An annular seal 102 is provided between the cylinder block 64 and the outer surface of the volume compensating piston 30 to prevent leakage of gas from the chamber 16.

As best seen in FIG. 4, the outer end of the volume compensating piston 30 has an axial bore 104 formed therein to receive the forward end of a micrometer operating shaft 106 which is secured within the bore 104 by a set screw 108. The micrometer operating shaft 106 extends axially forwardly or outwardly from a tubular portion 110 of the micrometer 32, the tubular portion 110 being threadedly secured within the micrometer support block and fixedly retained therein by a set screw 112. A support block 114 receives the outer end of the micrometer support tube 100 therethrough in supporting relation therewith, the support block 114 being suitably affixed to the base plate 66. The micrometer support tube 100 has a flange 116 thereon which is secured to the end surface of the cylinder block 64 by suitable screws 118.

The micrometer 32 is of known design, such as the commercially available Mitutoyo micrometer MHG 1-50 W2 Code No. 152-380 having a range of 0-50 mm in increments of 0.002 mm. Actuation of the micrometer 32 is operative to incrementally axially adjust the volume compensating piston 30 and provide a highly accurate determination of the displacement of the piston 30. The scale on the micrometer may read directly the change in volume of the chamber 16 upon each incremental adjustment of the micrometer, or may read a scale which requires conversion to obtain the volumetric displacement effected by movement of the piston 30.

The end of the chamber 18 opposite the piston 22 receives the dummy piston 40 in fixed position therein, the dummy piston being cylindrical and being secured at its outer end to a flange 122 through a screw 124, the flange 122 being secured to the cylinder block 64 by screws 126. The dummy piston 40 is of equal diameter to the volume compensating piston 30 and, as noted, is made from the same material as the volume compensating piston and pistons 20 and 22 so as to have the same thermal conductivity and reduce the temperature sensitivity of the apparatus.

With particular reference to FIGS. 3 and 4, the sample receiving chamber 28 and the chamber 38 are formed in the cylinder block 64 so as to intersect an upper surface 130 on the cylinder block. The chambers 28 and 38 are of identical cylindrical configuration and are symmetrical relative to the longitudinal axis of the cylinder block 64, with the axis of each chamber 28 and 38 preferably intersecting the axis of its associated underlying chamber 16 or 18. The cylinder block 64 has a pair of annular seal receiving grooves 132 and 134 formed in the upper surface 130 thereof each of which receives a conventional O-ring seal concentric with the cylindrical chambers 28 and 38, respectively. The cylinder block 64 has suitable tapped bores 136 (FIG. 3) formed in the upper surface 130 to facilitate attachment of a pair of identical chamber covers 138 and 140 onto the cylinder block, as by screws 142. Each of the chamber covers 138 and 140 has a central downwardly depending boss thereon, one of which is indicated at 144 in FIG. 4, which is snugly received within the underlying chamber 28 or 38.

The sample receiving chamber 28 is in communication with the chamber 16 through passages 150 and 152 formed in the cylinder block 64 and thus may be said to comprise a portion of the chamber 16. It will be understood that the sample receiving chamber 28 may take other configurations or that means may be provided to directly insert a sample within the chamber 16. Preferably, however, the separate sample chamber 28 is provided to facilitate sample manipulation and cleaning of the sample chamber.

The chamber 38 in the cylinder block 64 is in communication with its associated chamber 18 through passages 150' and 152' so as to establish a free space volume substantially equal to the combined free space volumes of the chambers 16 and 28. The passages 150 and 150' communicate with a cross passage 154 formed in a valve body plate 156 secured to the cylinder block 64 as by screws 158. The valve body plate 156 supports the equalizer valve 50 to facilitate control of gas flow through the ports 154 between the chambers 28 and 38. The valve body plate 156 has provision for 0-ring seals 160 to prevent gas leakage between the engaging surfaces of the valve body plate and cylinder block.

A second rectangularly shaped valve body plate 164 is mounted on the cylinder block 64 and guide block 68 through suitable screws 158. The valve body plate 164 supports the vent valve 52, the vacuum valve 54 and the gas valve 56 as shown in FIG. 3. The vent valve 52 is operative to vent the chambers 16, 18, 28 and 38 to atmosphere through a vent passage 166 and passages 168 and 170 when the equalizer valve 50 is open. The vacuum valve 54 facilitates selective connection of the chambers to a source of vacuum (not shown) through the passage 170, a suitable pipe thread opening 172 being provided for this purpose.

The gas valve 56 facilitates selective connection of the chambers 16, 18, 28 and 38 to a source of gas (not shown) through a pipe thread opening at 174 and through passages 176 and 178 communicating with the chamber 38. With the flow passage arrangement and valving as thus described, it can be seen that chambers 16, 18, 28 and 38 may be either cross vented to each other, vented to atmosphere, connected to a source of vacuum or connected to a source of gas through selective actuation of the control valves 50, 52, 54 and 56. It will be understood that the porting to sample chamber 28 may be varied as necessary to facilitate retention of a liquid sample therein.

The differential pressure transducer 46 is illustrated schematically in FIG. 2 as being connected to the chambers 16 and 18. In the embodiment of the pycnometer apparatus illustrated in FIGS. 3–5, the differential pressure transducer 46 is shown mounted on the valve body plate 156 and is suitably connected, as through ports 180 and 182, to the chambers 28 and 38 so as to continually monitor the differential pressure between the chambers 16, 28 and 18, 38. The differential pressure transducer 46 is connected to the differential pressure gauge 48 through conductors (not shown) in a known manner.

With the gas pycnometer apparatus 10 as described, the above described method for determining the volume of a condensed material substance may be readily carried out. With the chamber covers 138 and 140 secured on the cylinder block 64 and with the valves 50, 52, 54 and 56 is closed positions after venting the chambers to atmosphere or preferably introducing helium gas into the chambers, the pistons 20 and 22 may be moved axially within their respective chambers 16 and 18 by rotation of the hand crank 96. By moving the pistons 20 and 22 equal distances between outward and inward positions within their respective chambers as determined by the stop surfaces 64a and 68a, cross venting the chambers and adjusting of the volume compensating piston 30 as aforedescribed to maintain zero pressure differential between the chambers throughout movement of the pistons 20 and 22, equal free space volumes are established between the chambers 16, 28 and 18, 38. After equal free space volumes are established between the chambers without a sample disposed within the sample receiving chamber 28, the sample cover 138 is removed and a condensed material sample is placed within the chamber 28. Thereafter, the pistons 20 and 22 are again moved between outward and inward position stops within their respective chambers 16 and 18 and the chambers are cross vented and the volume compensating piston 30 is adjusted as necessary to maintain equal pressure within the chambers and again establish equal free space volumes between the chambers in the same manner as when no sample was disposed within the sample receiving chamber 28.

The incremental adjustment of the volume compensating piston 30 necessary to reestablished equal free space volumes between the chambers 16, 28 and 18, 38 provides a highly accurate determination of the volume of the solid or powder sample 26 under the same conditions as existed within the chambers when the sample was not disposed within the sample receiving chamber; namely, under conditions wherein equal free space volumes and thus the same number of moles of gas existed within the chambers. From this highly accurate determination of the volume of the sample 26, the density of the sample may be accurately inferred by either previous or subsequent weighting of the sample. Commercially available balances are capable of weighting a sample, such as the sample 26, with a precision greater than 1 part in 10,000. Such weight determination, coupled with the highly accurate volume determination obtainable with the pycnometer apparatus 10 of the present invention, i.e. $\pm$ 0.001 cc, allows density determinations of $\pm$ 0.002 gm.cc or better to be inferred.

Significant advantages are provided by the gas comparison pycnometer apparatus 10 in accordance with the present invention as follows. Firstly, the pycnometer apparatus 10 does not require that the ideal gas law be precisely obeyed. Any departure from ideality of the gas being used does not result directly in an uncertainty in the inferred volume as exists in the known prior art gas comparison pycnometers. The pycnometer apparatus 10 of the present invention is stable against thermal variations which, in the prior gas comparison pycnometers, can influence the pressure measured in the sample chamber and cause a spurious variation in the measured volume. Additionally, in the prior gas comparison pycnometers, the number of moles of gas in the sample and reference chambers is different when the apparatus are in balanced or zeroed conditions and when a sample is present. In accordance with the gas comparison pycnometer apparatus of the present invention, the number of moles of gas is equal in both of the chambers both before and after a sample is inserted within the sample receiving chamber.

In addition to providing a highly accurate measurement of the volume of a solid or powder sample, the gas comparison pycnometer apparatus 10 also lends itself to hydrostatic pressurization of the sample chamber. By increasing the ambient pressure in the chambers 16, 28 and 18, 38 and then performing a volume measurement, the apparatus 10 can be used to measure sample volume as a function of pressure, and hence measure the compressibility or modulus of elasticity of compressible substances. The apparatus 10 may be employed to determine the connected porosity of a material sample by first encasing the sample in a membrane and measuring the combined volume, and thereafter measuring the removed membrane and the sample combined volume, the difference being the connected pore volume. The unconnected pore volume may be determined by then crushing the sample and again measuring the membrane and the sample powder volume. The difference between the latter volumes is the closed pore volume.

Additionally, the apparatus 10 may be employed to determine the connected pore size distribution of a sintered material sampler by first measuring the volume of the sample as aforedescribed with a first gas the molecules of which are of a size insufficient to enter the pores within the sintered material, and thereafter measuring the volume of the sample by use of a gas the molecules of which are of a size sufficient to enter into all of the internal voids within the sintered material sample. A comparison of the volumes so calculated by use of the two gases provides a measure of volume of pores connected by gas-molecule size interconnections in the material sample.

While a preferred method of determining the volume of a solid or powder sample and a preferred embodiment of a gas pycnometer apparatus for carrying out the volume determination in accordance with the present invention have been illustrated and described, it will be apparent to those skilled in the art that changes and modifications may be made therein without departing from the invention in its broader aspects. Various features of the invention are set forth in the following claims.

What is claimed is:

1. A gas comparison pycnometer apparatus comprising housing means defining a pair of substantially equal volume chambers, said chambers being adapted to receive a gas therein, primary means operatively associated with each of said chambers and selectively operable to vary the free space volumes within said chambers, at least one of said chambers being adapted to receive a condensed material sample therein, auxiliary piston means operatively associated with said sample receiving chamber and incrementally adjustable to selectively vary the free space volume of said sample receiving chamber independently of said primary means, means for effecting selective communication between said pair of chambers to facilitate equalization of gas pressure therebetween, differential pressure measuring means communicating with each of said chambers and adapted to indicate the differential pressure between said chambers, said auxiliary piston means including measuring means adapted to indicate the incremental change in free space volume of said sample receiving chamber effected by incremental adjustment of said auxiliary piston means, and dummy piston means operatively associated with the other of said chambers and having thermal conductivity characteristics substantially identical to said auxiliary piston means.

2. A pycnometer apparatus as defined in claim 1 wherein said primary means comprises a primary piston disposed within each of said chambers, said primary pistons being of equal size and axially movable within said chambers to vary the free space volumes thereof, said auxiliary piston means comprising an auxiliary piston operatively assiciated with said sample receiving chamber and axially movable to selectively vary the free space volume of said sample receiving chamber independently of said primary pistons, said primary pistons being made of material having identical thermal conductivity as said dummy and auxiliary piston means.

3. A pycnometer apparatus as defined in claim 2 wherein said auxiliary piston is adapted to intrude into said sample receiving chamber, and wherein said dummy piston means intrudes the other of said chambers, said auxiliary piston and said dummy piston means and their respective chambers being symmetrically disposed relative to the longitudinal axis of said housing means.

4. A pycnometer apparatus as defined in claim 2 wherein said chambers and associated primary pistons are symmetrical relative to the longitudinal axis of said housing means so as to provide thermal symmetry between said chambers.

5. A pycnometer apparatus as defined in claim 1 including means facilitating selective connection of said chambers to atmosphere, a vacuum or to a predetermined gas other than air.

6. A pycnometer apparatus as defined in claim 2 including means cooperative with said primary pistons to effect simultaneous movement thereof.

7. A pycnometer apparatus as defined in claim 1 wherein said housing means includes an integral cylinder block having relatively high thermal conductivity, said chambers comprising cylindrical bores formed in said cylinder block and having substantially equal diemeters, the longitudinal axes of said bores being parallel to and equidistantly spaced from the longitudinal axis of said cylinder block.

8. A pycnometer apparatus as defined in claim 7 wherein said cylinder block is made of aluminum, and wherein said primary means, said auxiliary piston means and said dummy piston means are made of stainless steel.

* * * * *

UNITED STATES PATENT AND TRADEMARK OFFICE
CERTIFICATE OF CORRECTION

PATENT NO. : 4,083,228
DATED : April 11, 1978
INVENTOR(S) : Philip L. Turner, et al.

It is certified that error appears in the above-identified patent and that said Letters Patent are hereby corrected as shown below:

Col 1. line 33, "amountes" should be --amounts--.

Col. 2, line 11, "of" second occurrence, should be --or--.

Col. 10, line 37, "weighting" should be --weighing--.

Col. 10, line 38, "weighting" should be --weighing--.

Col. 10, line 44, "gm.cc" should be --gm/cc--.

Col. 11, line 1, "chamber" should be -- chambers --.

Col. 11, line 19, "sampler" should be --sample--.

Col. 12, line 16, "assiciated" should be --associated--.

Col. 12, line 47, "diemeters" should be --diameters--.

Signed and Sealed this

Tenth Day of October 1978

[SEAL]

Attest:

RUTH C. MASON
Attesting Officer

DONALD W. BANNER
Commissioner of Patents and Trademarks